(12) United States Patent
Chen et al.

(10) Patent No.: US 6,500,539 B1
(45) Date of Patent: Dec. 31, 2002

(54) ANTI-ADHESION CELLULOSE ACETATE WOUND DRESSING

(75) Inventors: John C. Chen; Kevin J. Soden, both of Charlotte, NC (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/035,484

(22) Filed: Mar. 5, 1998

(51) Int. Cl.⁷ .............................. D02G 3/00; A61F 13/00
(52) U.S. Cl. .............................. 428/364; 602/41; 602/54
(58) Field of Search ....................... 602/41–59; 129/888, 129/889; 428/364, 290, 306.6, 308.4, 315.5, 907; 442/76, 152, 123, 153, 164; 604/367, 374, 372, 377; 424/443–448

(56) References Cited

U.S. PATENT DOCUMENTS

| | | | |
|---|---|---|---|
| 3,285,245 A | 11/1966 | Eldredge et al. | |
| 3,959,556 A | 5/1976 | Morrison | 428/364 |
| 4,343,853 A | 8/1982 | Morrison | 428/233 |
| 4,546,027 A | 10/1985 | Holvoet et al. | 428/109 |
| 4,595,001 A | 6/1986 | Potter et al. | 128/156 |
| 4,984,570 A | 1/1991 | Langen et al. | 128/156 |
| 5,372,739 A | 12/1994 | Neal et al. | 252/8.6 |
| 5,635,201 A | 6/1997 | Fabo | 424/443 |
| 5,685,832 A | 11/1997 | Chen et al. | 602/48 |
| 5,856,245 A * | 1/1999 | Caldwell et al. | 442/76 |
| 5,910,368 A | 6/1999 | Ehret | |

FOREIGN PATENT DOCUMENTS

| | | |
|---|---|---|
| CN | 87101823 A | 8/1988 |
| DE | 20 07 449 A | 12/1970 |
| DE | 41 36 540 A | 5/1992 |
| EP | 0 342 950 A | 11/1989 |
| FR | 1 151 199 A | 1/1958 |
| GB | 898 826 A | 5/1959 |
| GB | 1 246 134 A | 9/1971 |
| WO | WO 89/01346 * | 2/1989 |

OTHER PUBLICATIONS

"Encyclopedia of Chemical Technology", 4th Ed. (Wiley–Interscience, John Wiley & Sons, New York) vol. 10, pp. 204–253, 598–624, 696–726.

* cited by examiner

Primary Examiner—Kim M. Lewis
(74) Attorney, Agent, or Firm—Greer, Burns & Crain, Ltd.

(57) ABSTRACT

A unique fabric with non-adherent characteristics making it suitable for use as a wound dressing, and particularly as a dressing for burns, is disclosed The fabric comprises cellulose acetate fibers and a siloxane finishing on the fibers. In a preferred embodiment, the dressing comprises cellulose acetate fibers, cellulose acetate fiber having an anti-biologic incorporated into the fiber resin, and a siloxane finishing on the fibers. The fabric of the invention was found to be less adherent to burns than dressings made from cotton or having a nylon net about an absorbent pad.

13 Claims, No Drawings

ANTI-ADHESION CELLULOSE ACETATE WOUND DRESSING

FIELD OF THE INVENTION

The invention is directed to a cellulose acetate anti-adhesion wound pad or dressing, and in particular to a cellulose acetate anti-adhesion pad having a low level of siloxane finishing agent applied thereto. The pad has use in the medical arts area for application to wounds, particularly burns.

BACKGROUND OF THE INVENTION

Numerous injuries, and particularly burns, require the application of some type of pad, gauze, cloth, dressing or similar covering (herein collectively called a "dressing") to protect the wound while it is healing. Wounds, especially burns, sometimes have difficulty in healing and are frequently prone to infection because natural protective skin barriers are disrupted and are slow in repairing themselves. The most commonly used dressing material has been cotton because it is both inexpensive and readily available. However, as those who have used cotton dressings are aware, they tend to stick to the injured area, even when the surface of the area is covered with a lubricant such as petroleum jelly ("petrolatum") or similar substance, or a medicinal which contains a lubricant. Developments in the medical arts have resulted in some improvements in medical dressings, two of which are represented by Johnson & Johnson's ADAPCTIC™ brand non-adherent dressings and the Curity® brand TELFA® sterile pads sold by Kendall-Futuro Company. The ADAPTIC™ brand dressing was found to consist of a cellulose acetate pad which has been soaked in petrolatum or similar substance to impart anti-adhesion properties. While the petrolatum reduces adhesion to a wound, it's use results in a pad that is greasy and messy to handle compared to a pad without petrolatum. The TELFA® dressing consists of a polyethylene terephthalate (PET) shell and a caustic washed cotton insert, the anti-adhesion properties being imparted by the PET shell.

Another dressing is disclosed in China Patent No. CN 87 1 01823 A, published Aug. 31, 1988, to Tie Han et al. This Chinese patent describes a "Medicinal Anti-Adhesive Dressing" prepared using plain cellulose acetate to make a spun and woven gauze, or a nonwoven fabric having a weight of 50–80 g/m$^2$. No additional information is given concerning treatment of the cellulose acetate material before, during or after preparation of the dressing. The dressing did not contain a biostat nor was use of a biostat suggested.

United States patents disclosing the use of cellulosic materials and siloxane materials in wound dressing include:

U.S. Pat. No. 5,372,739 to B. Shriram which describes fibers, including cellulose acetate fibers, having polyethylene glycol fatty acids thereon to reduce adhesion;

U.S. Pat. No. 4,984,570 to Langen et al. which describes a wound dressing having a cellulose acetate absorbent pad and a hydrophobic man-made fiber covering over the pad which covering is in contact with the wound;

U.S. Pat. No. 4,546,027 to Holvoet which describes the use of a nonwoven corrugated fabric for medical and surgical compresses, which compresses include the use of plastic reinforced cellulose fibers;

U.S. Pat. No. 5,635,201 to Fabo which describes the use of a curable siloxane material coated on a carrier surface and heat cured to form a siloxane gel; and U.S. Pat. No. 5,685,832 to Chen et al. which describes a wound dressing comprising a woven cellulose acetate substrate and a partial solvent thereon, which dressing releases, in a controlled manner, acetic acid to act as a therapeutic agent.

U.S. Pat. No. 3,285,245 to Eldridge et al. which describes an absorbent wound dressing having an absorbent backing and a non-absorbent facing.

These dressing, while having various qualities which may reduce adhesion or provide other benefits, incorporate lubricants and/or fluids or fluid releasing agents, and use fibers other than cellulose acetate to provide non-adhesion properties.

Adhesive dressings and methods of preparing adhesive dressings are well known in the art as exemplified by U.S. Pat. No. 4,595,001, and patent references cited therein, to Potter (a surgical dressing which carries an adhesive layer for securing a dressing to a body), all of whose teachings are incorporated herein by reference.

While the above dressings represent improvements in reducing dressing adhesion to wounds, further improvements in the field is highly desirous. In particular, an improved dressing of cellulose acetate would useful in the medical arts because cellulose acetate is both chemotactic for attracting white blood cells and hydrophilic. The white cell chemotactic property of cellulose acetate fibers is desirable in a wound dressing because white blood cells aid in fighting infection. The hydrophilic property is desirable because it aids in removing excess fluids which may ooze from the surface of a wound during the healing process. Accordingly, the present invention is directed to providing such improved dressing.

It is an object of the invention to provide a wound dressing made of cellulose acetate which has improved non-adhesion characteristics.

It is a further object of the invention to provide a wound dressing made of cellulose acetate and a low level of a siloxane finishing agent, which dressing has improved non-adhesion characteristics.

It is an object of the invention to provide a self-adhesive bandage having a wound dressing pad attached thereto, which pad is made of cellulose acetate with or without a low level of a siloxane finishing agent, and which pad has improved non-adhesion characteristics.

It is an additional object of the invention to provide a biostat containing wound dressing and/or self-adhesive bandage having a wound dressing attached thereto, which dressing is comprised in part or wholly of cellulose acetate, and has a low level of a siloxane finishing agent applied thereto; and which dressing has improved non-adhesion characteristics.

SUMMARY OF THE INVENTION

The invention is directed to a wound dressing which does not adhere to a wound surface or which has improved non-adhesion characteristics relative to the wound dressings known to the art. In the one embodiment, the invention comprises a woven or non-woven cellulose acetate dressing. In a preferred embodiment, the invention comprises a non-woven cellulose acetate web, and a particularly preferred nonwoven dressing comprises a spunlace material having a weight of about 20 to about 90 g/m$^2$ (grams per square meter). These embodiments can further comprise such additional substances as low levels of siloxane materials to finish the dressing or the fibers used to make the dressing and additionally impart further adhesion-reduction characteristics; and anti-bilogics such as bactericides and fungicides which can be incorporated into the cellulose acetate before if is formed into a filament for use in producing the dressing or such anti-biologics incorporated into a fiber which can be used in conjunction with cellulose acetate fibers to produce the dressing.

In another embodiment, the invention is directed to an article of manufacture comprising an adhesive strip having an adhesive on one side thereof and a wound dressing adhering to a portion of the adhesive side of said strip, wherein said wound dressing comprises one or a plurality of layers of a fabric comprising cellulose acetate fibers, biostat-containing cellulose acetate fibers having a biostat content of about 1% to about 5%, and a siloxane in the amount of about 0.01% to about 0.0001%; wherein the amount of biostat-containing fibers in the dressing is from about 1% to about 100% of the total fiber in the dressing.

DETAILED DESCRIPTION OF THE INVENTION

The term "anti-biologic" or "biostat", and variations thereof, as used herein means any substance which has an effect on a biological organism, and in particular means bactericides, antibiotics, fungicides, herbicides, antimicrobials and similar substances which effect biological organisms, both animal and plant.

The term "dressing" as used herein means any material applied to protect, cushion, cover, and generally guard a wound from either further injury or from any desirable contacts. The material may be in any form such as a pad, gauze, cloth, sheet, or similar form as night be used in the medical arts. The dressing may be used by itself or in conjunction with a medicinal or other substance applied thereto or contained therein, and may comprise multiple layers of the cellulose acetate materials of which the dressing is made.

The terms "non-stick," "no-stick," "anti-adherent," "non-adherent", "anti-adhesion" and variations thereof, and similar terms, may be used interchangeably to signify a dressing which either does not stick or adhere to a wound, or which exhibits a reduced tendency to stick or adhere to a wound relative to other dressings.

The dressing may be made of either a woven or a nonwoven cellulose acetate; nonwoven being preferred. Further, the dressing may be made of cellulose acetate alone or in combination with another filament or fiber suitable for use in medical dressings, including polyesters, polyolefins, polyamides and cotton; polyesters being preferred.

All percentages herein are weight percentages unless specified otherwise.

General Preparative Methods

The cellulose acetate containing dressing of the invention may be either a woven or nonwoven material, nonwoven being preferred. The spinning process used to produce a cellulose acetate dressing can be either dry spinning or wet spinning as those terms are understood by one skilled in the art. A description of cellulose acetate filaments and fibers (hereafter collectively called "fibers"), and the materials and processes used to make such fibers, can be found in the "Encyclopedia of Chemical Technology, 4th Ed." (Wiley-Interscience, John Wiley & Sons, New York), Vol. 10, pages 204–253 (nonwoven fabrics), 598–624 (cellulose esters) and 696–726 (regenerated cellulosics), and are well known to those skilled in the art.

The process used to incorporate anti-biologics into a fiber is well known in the art as exemplified by U.S. Pat. Nos. 3,959,556 and 4,343,853 to Morrison which describe incorporating an antimicrobial agent into a thermoplastic resin to produce a fiber having the antimicrobial intimately mixed with the resin. Cellulose acetate is a thermoplastic substance.

Woven fabrics can be prepared using cellulose acetate fibers by conventional weaving procedures known to those skilled in the art. Such techniques can be used to produce either a cellulose acetate (only) fabric or a fabric comprising cellulose acetate and a second fiber having an anti-biologic intimately mixed with the fiber resin.

Nonwoven fabrics can be prepared using cellulose acetate fibers by conventional nonwoven techniques known to those skilled in the art. In the preferred embodiment of the invention the nonwoven fabric is prepared according to the spunlace method. The spunlace method can be used to produce either a cellulose acetate (only) fabric or a fabric comprising cellulose acetate and a second fiber having an anti-biologic intimately mixed with the fiber. In the preferred embodiment the anti-biologic containing fiber is cellulose acetate and the anti-biologic containing fiber is present in the fabric in an amount of greater than zero pecent to 100% of the total fiber of the fabric.

The fibers used to produce woven or nonwoven fabric are made using spinnerets having 50 to about 250 openings therein for producing filaments of about 1 to about 50 denier per filament (dpf), with 1–5 dpf being preferred. Heavier dpf materials are used when multiple "layers" are desired in a nonwoven fabric, for example, for strength imparted by a layer of heavier fibers, or when it is desired to give any fabric more "body." The fabrics, and particularly the spunlace fabric, are produced in a weight range of about 20 to about 90 g/m$^2$. After fabric forming, the fabric is then needled or punched to yield a fabric having from about 10 to about 200 openings per square centimeter. Alternatively, the fabric may be used as formed and not punched or needled to form openings. Subsequent to fabric forming and needling, the fabric may under go optional additional treatments such as washings. In preferred embodiments of the invention, the fabric was washed and treated with a siloxane containing solution comprising 2.27 kilograms (Kg) of 70% Sentry NF30 and 30% Nuwet 500 (both from Witco Chemicals, Greenwich, Conn., USA) in about 226 liters of deionized or distilled water (5 lbs per 60 gallons). Those skilled in the art are familiar with the foregoing siloxane materials and the invention hereby teaches that similar silicone materials from other sources can be substituted. Siloxane treatment time was in the range of 10–30 minutes, and with about 15 minutes being a typical treatment time. Following siloxane treatment the fabric was optionally water washed to remove excess silicone and dried The amount of siloxane on the fabric after washing, if any, and drying is from about 0.01% to about 0.0001%. The fabric may then be folded, cut and otherwise processed and packaged for sale to the end user. Fabric was sterilized by any sterilization method known in the art, for example, by gamma irradiation whereby 27–34 KGy was delivered. When applied to wounds, a dressing may consist of one or more layers of the fabric of the invention. Typically, one to twenty layers maybe use, the exact number being determined by the nature and/or severity of the wound.

EXAMPLE 1

Cellulose Acetate Fabric Containing Sloxane and No Biostat

Using the general procedures described above, 3 dpf filaments were extruded from a plurality of spinnerets to produce a fiber subsequently us ed in the spunlace method to produce a nonwoven fabric of 77 g/m² weight with about 24 openings per square centimeter. The fabric was washed, treated with the siloxane solution, dried, packaged and sterilized using gamma radiation. Alternatively, a fabric can be prepared by conventional weaving using spun yarn from cellulose acetate staple, e.g., a 1×1 plain weave pattern at comparable fabric weight.

EXAMPLE 2

Cellulose Acetate Fabric Containing Siloxane and a Biostat

Using the general procedures described above, 3 dpf fibers were extruded from spinnerets, and the resulting fibers used to produce a nonwoven spunlace fabric of 77 g/m² weight. One or a plurality of fibers used in producing the fabric was a fiber containing the biostat Microban® [2,4,4'-trichloro-2'-hydroxydiphenyl ether, or alternatively, 5-chloro-2(2,4-dichlorophenoxy)phenol], a chlorinated phenoxy material identical to one of those disclosed in the Morrison patents. The Microban® containing fiber used in preparing the fabric of this Example was Mcrosafe® cellulose acetate fiber available from Celanese Acetate LLC, Charlotte, N.C., U.S.A. Other biostat fibers useful in practicing the invention includes polyolefin, polyamide, polyester, polyacrylate, polyvinyl alcohol and similar fibers known to those skilled in the art. Generally, the biostat may be incorporated into the fabric resin in an amount of about 0.01% to about 5%. A s used in this Example, the biostat amount incorporated into the fiber was about 2%.

The amount of biostat-containing fiber incorporated into a woven or nonwoven fabric may be from about 1% to 100%. Preferably, the amount may be from about 1% to about 50% and most preferably from about 3% to about 30%. As used in this Example, 2 to prepare the CAM dressing below the amount of biostat-containing fiber in the spunlace fabric was about 30%. The needled fabric was washed, treated with the siloxane solution, dried, packaged and sterilized using gamma radiation.

Field Tests

Field tests were conducted at four hospitals in China, all major burn centers, because burns are a common occurrence in China where kerosene heaters are commonly used for indoor heating during the winter months and open fires are used for cooking year around. As a result, an evaluation of the dressing of the invention and other dressings could be made more quickly because of a readily available pool of patients. In addition, because of cost consideration, dressings are generally left on the burns for longer periods of time before they are changed, unless medical necessity or circumstances dictate otherwise.

The Clinical Directors of each hospital burn center were asked to help design a single study protocol that would be used to evaluate the dressing of the invention against other burn dressings commonly used in China.

Four different dressings were used in the field tests. These are:

1. Cotton gauze;
2. Kangda, a commercially available dressing in China
3. CAYX a commercially available "plain" cellulose acetate dressing from Yong Xing Company; and
4. CAM, the cellulose acetate dressing of the invention prepared according to Example 2.

The Kangda dressing is a nylon netting having cotton stuffing. The CAYX dressing is "plain" cellulose acetate having no discernible other material such as petrolatum, siloxane or biostat, and is similar to that of China published patent 87 1 01823 A cited above. The CAM dressing was prepared according to Example 2.

The dressings were applied in a standardized manner to a sufficiently large body area on each patient which would accommodate all four dressings. A drawing was made of each burn site on the patient evaluation sheet to record the order of application and the location of each dressing. Each dressing sample was a minimum of 10×10 cm² and sixteen (16) layers thick. Prior to placing the dressing on the burn surface, a thin layer of Silvadene cream was applied to either the burn site or the dressing. The Silvadene was reapplied at each subsequent dressing change. After application, the dressings were overlapped with a standard material such as cotton gauze in order to hold the dressing in place.

To minimize any differences which might be caused by having multiple physician evaluators, each Field Test site designated one physician to be the primary evaluator who would complete the Patient Evaluation form. This form was completed at every dressing change by the primary examining physician. Dressings were initially changed after 24 hours, and the changing was later extended to 48 hours as the wounds healed. Each dressing change results in a separate Evaluation.

The participants were patients who were hospitalized with a minimum of second degree burns on less than 50% of the body. The patients were between 15 and 55 years of age and were free from any medical conditions such a diabetes, HIV and other immunosuppressed conditions that would effect wound healing. A target number of 30 participants of either sex were selected for the field test at each hospital site. A total of 270 patients from all hospital sites were collected in the trials. The Field Test Results are given in Tables 1–5.

Pain was evaluated using a 1–10 scale with one (1) being no pain and ten (10) being the worst pain. Adherence was also evaluated using a 1–10 scale with one (1) being no adhesion and ten (10) signifying that the dressing was stuck to the wound. Wound appearance was evaluated using a scale of 10–100, with 100 indicating worst appearance.

TABLE 1

Pain Scores. N = 270 Patient Encounters

| Dressing | Average Score | "P" Value vs. Cotton |
|---|---|---|
| Cotton | 4.01 | — |
| Kangda | 2.89 | — |
| CAYX | 2.70 | — |
| CAM | 2.02 | <0.01 |

TABLE 2

Pain Scores by Hospital

| Hospital | No. Readings | Cotton | CAM | "P" Value |
|---|---|---|---|---|
| Shanghai | 53 | 2.40 | 1.55 | <0.05 |
| 304th Military | 37 | 3.27 | 1.43 | <0.01 |
| Ji-Shui | 120 | 4.40 | 2.52 | <0.01 |
| Rui Tan | 52 | 5.54 | 1.88 | 0.01 |

The results of Table 1, Pain, indicate that the CAM dressing containing Microsafe® fibers and having a siloxane treatment caused significantly less pain when removed than any of the other dressings. The CAM dressing had an average score of 2.02 out of a total of 262 readings (dressing changes) in contrast to an average score of 2.70 for the next best dressing, CAYX. The Pain Score for CATX, the plain cellulose acetate dressing was about 35% higher than that of CAM, the dressing of the invention. Cotton dressing had the highest pain score, about double that of CAM. There were no difference in the results when the age and sex of the patients was considered.

The overall trend in scores remained consistent when the scores were separated by participating hospital as shown in Table 2, indicating that the statistical data is accurate and that there were no anomalies.

TABLE 3

Wound Adherence Scores (N = 270 Patient Encounters)

| Dressing | Adherence Average | "P" Value vs. Cotton |
|---|---|---|
| Cotton | 4.13 | — |
| Kangda | 2.93 | — |
| CAYX | 2.83 | — |
| CAM | 2.01 | <0.01 |

TABLE 4

Wound Adherence Scores By Hospital

| Hospital | No. Readings | Cotton | CAM | "P" Value |
|---|---|---|---|---|
| Shanghai | 53 | 2.32 | 1.51 | <0.05 |
| 304th Military | 37 | 3.95 | 1.43 | <0.01 |
| Ji-Shui Tan | 120 | 4.67 | 2.60 | <0.01 |
| Rui Tan | 52 | 5.29 | 1.75 | <0.01 |

The results of Table 3, Adherence Scores, indicate that the CAM dressing containing Microsafe® fibers and having a silicone treatment was significantly less adherent to a wound than any of the other dressings. The CAM dressing had an average score of 2.01 out of a total of 262 readings (dressing changes) in contrast to an average score of 2.83 for the next best dressing, CAYX. The Adherence Score for CAYX, the pain cellulose dressing, is about 40% higher than that of CAM, the cellulose acetate dressing of the invention. Cotton dressing had the highest adherence score, about double that of CAM. There were no differences in the results when the age and sex of the patients was considered.

The overall trend in scores remained consistent when the scores were separated by participating hospital as shown in Table 4, indicating that the statistical data is accurate and that there were no anomalies.

TABLE 5

Wound Appearance Scores

| Dressing | Average Score | "P" Value vs. Cotton |
|---|---|---|
| Cotton | 25.60 | — |
| Kangda | 23.54 | — |
| CAYX | 20.25 | — |
| CAM | 18.58 | <0.05 |

While judging the appearance of wounds is often very subjective, but the clinicians involved in the study wished to include this as one of the factors being evaluated. Appearance was judged after the dressings were removed and were assessed on the amount of healthy appearing wound surface observed. The greater the amount of healthy wound surface observed, the lower the score.

The results of Table 5, Wound Appearance Score, indicate that the CAM dressing containing Microsafe® fibers and having a siloxane treatment resulted in the lowest score and hence was deemed indicative that the wound was healing properly. The CAM dressing had an average score of 18.58 in contrast to an average score of 20.225 for the next best dressing, CAYX. Cotton dressing had an Appearance Score of 25.60. There were no difference in the results when the age and sex of the patients was considered.

If an ideal wound dressing could be designed, it would protect the wound surface, while not disturbing the healthy granulating tissue when removed, absorb blood and other fluids, help promote wound healing by chemotaxis of leukocytes, reduce the overall risk of infection and be inexpensive when compared to other commercially available dressings. While cotton has long been the standard dressing for use in burns and other healing wounds, largely due to its availability and low cost, it does not of itself promote the healing process. Microscopically, cotton is a fiber that possesses an irregular surface with numerous tiny protuberances on the surface of the fiber. It is these protuberances that cause cotton fibers to stick uncomfortably to a wound's surface. In contrast, cellulose acetate dressings, and in particular the CAM dressing described herein, possess advantages over cotton. Cellulose acetate fibers generally have a smooth surface without breaks or protuberances to catch in a wound surface. In view of this fact, it is not surprising that cellulose acetate is less adhesive than cotton or other materials.

It is noted that although both the CAYX and CAM dressings are made of a cellulose acetate fabric, the CAM dressing of the invention is superior to the CAYX in all categories. Without being held to any particular theory or explanation, this is believed to the result of CAM including both a biostat and a siloxane.

While this invention has been described with an emphasis on the preferred embodiments, it will be apparent to one of ordinary skill in the art that variations of the preferred embodiments can be used and it is intended that the invention can be practiced otherwise than as specifically described herein, in both the medical and non-medical arts. For example, in a non-medical art application, a herbicide can be used in of a antimicrobial agent, seeds can be implaced in the fabric and the fabric placed in the ground to facilitate gardening, particularly for the home gardener. The cellulose acetate fabric will aid in retarding moisture loss from the soil as well as placing seed in the proper location and providing for the release of the herbicide. In the medical field, polyester or polyolefin fibers contains biostat as indicated herein could be used in lace of the biostat-containing cellulose acetate fibers. Additionally, one could increase the amount of siloxane on the the would dressing to be within the range of 0.0001% to about 2% by various methods such as by grafting a siloxane to the fibers according to methods known to those skilled in the art or as taught in U.S. Patent to Fabo cited above. Accordingly, this invention includes all modifications encompassed within the scope and spirit of the invention as defined by the following claims.

We claim:

1. A fabric comprising cellulose acetate fibers, cellulose acetate fibers having a selected quantity of a biostat therein, and a siloxane; wherein the biostat-containing fibers are from about 1% to about 100% of the fibers in the fabric, the siloxane is from about 0.01% to about 0.0001% and said fabric is selected from the group consisting of knitted woven and nonwoven fabrics.

2. The fabric according to claim 1 wherein the quantity of biostat-containing fibers in the fabric is in the range of about 1% to about 50%.

3. The fabric according to claim 2, wherein the quantity of biostat-containing fibers in the fabric is in the range of about 3% to about 30%.

4. The fabric according to claim 1, wherein the biostat content of the biostat-containing fibers is from about 0.0% to about 5%.

5. The fabric according to claim 1, wherein said fabric is a non woven fabric, said biostat-containing fibers are from about 3% to about 30% of the total fibers, and said biostat-containing fibers contain from about 0.01% to about 5% biostat.

6. The fabric according to claim 5, wherein said fabric is a spunlace fabric.

7. The fabric according to claim 5, wherein the cellulose acetate and biostat-containing cellulose acetate fiber are from about 1 to about 50 dpf.

8. The fabric according to claim 5, wherein the cellulose acetate and biostat-containing cellulose acetate fiber are from about 1 to about 5 dpf.

9. The fabric according to claim 8, wherein the fabric is a spunlace fabric.

10. The fabric according to claim 1, wherein the cellulose acetate and biostat-containing cellulose acetate fiber are from about 1 to about 50 dpf.

11. The fabric according to claim 1, wherein the cellulose acetate and biostat-containing cellulose acetate fiber are from about 1 to about 5 dpf.

12. An anti-adherent wound dressing comprising a fabric of (a) cellulose acetate fibers and cellulose acetate fibers having a selected quantity of a biostat therein; and (b) a siloxane applied to said fabric;

wherein:

(i) the biostat-containing fibers are present in an amount of from about 1% 100% of the total fibers and the biostat content of the biostat-containing fibers is from about 0.01% to about 5%;

(ii) both the cellulose acetate and biostat-containing cellulose acetate fibers are from about 1 to about 50 dpf, (iii) the silicone is from about 0.01% to about 0.0001%.

13. An article of manufacture comprising an adhesive strip having an adhesive on one side thereof and a wound dressing adhering to a portion of the adhesive side of said strip, wherein said wound dressing comprises one or a plurality of layers of a fabric comprising cellulose acetate fibers, biostat-containing cellulose acetate fibers having a biostat content of about 1% to about 5%, and a siloxane in the amount of about 0.01% to about 0.0001%;

wherein the amount of biostat-containing fibers in the dressing is from about 1% to about 100% of the total fiber in the dressing.

* * * * *

UNITED STATES PATENT AND TRADEMARK OFFICE
CERTIFICATE OF CORRECTION

PATENT NO. : 6,500,539 B1
DATED : December 31, 2002
INVENTOR(S) : Chen et al.

It is certified that error appears in the above-identified patent and that said Letters Patent is hereby corrected as shown below:

<u>Title page,</u>
Item [57], ABSTRACT,
Line 10, delete "." at end of paragraph and insert -- , and was also less adherent than a commercially available cellulose acetate dressing. --.

Signed and Sealed this

Fifteenth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,500,539 B1
DATED : December 31, 2002
INVENTOR(S) : Chen et al.

It is certified that error appears in the above-identified patent and that said Letters Patent is hereby corrected as shown below:

Column 2,
Line 9, replace "dressing," with -- dressings --.

Column 3,
Line 2, replace "if" with -- it --.

Column 4,
Line 59, replace "maybe use," with -- may be used, --.

Column 7,
Line 1, replace "CATX" with -- CAYX --.
Line 59, delete "but".

Column 8,
Line 5, replace "difference" with -- differences --.
Line 45, replace "lace" with -- place --.

Column 9,
Line 2, replace "0.0%" with -- 0.01 --.
Lines 11 and 14, replace "claim 5" with -- claim 1 --.

Signed and Sealed this

Twenty-fifth Day of April, 2006

JON W. DUDAS
*Director of the United States Patent and Trademark Office*